United States Patent
Agee et al.

(10) Patent No.: US 6,277,338 B1
(45) Date of Patent: Aug. 21, 2001

(54) SYSTEM FOR CONVERTING LIGHT HYDROCARBONS TO HEAVIER HYDROCARBONS WITH SEPARATION OF WATER INTO OXYGEN AND HYDROGEN

(75) Inventors: Mark A. Agee; Larry J. Weick, both of Tulsa, OK (US)

(73) Assignee: Syntroleum Corporation, Tulsa, OK (US)

( * ) Notice: Subject to any disclaimer, the term of this patent is extended or adjusted under 35 U.S.C. 154(b) by 0 days.

(21) Appl. No.: 09/429,591

(22) Filed: Oct. 28, 1999

Related U.S. Application Data (62) Division of application No. 09/168,195, filed on Oct. 7, 1998, now Pat. No. 6,011,073.
(60) Provisional application No. 60/061,666, filed on Oct. 10, 1997.

(51) Int. Cl.[7] .......................................................... B01J 8/04
(52) U.S. Cl. .......................... 422/189; 422/190; 422/211; 423/580.1; 423/648.1; 423/657; 518/702; 518/703; 518/704; 518/705
(58) Field of Search ..................................... 518/702, 703, 518/704, 705; 422/190, 211, 187, 188, 189; 423/580.1, 648.1, 657

(56) References Cited

U.S. PATENT DOCUMENTS

| | | |
|---|---|---|
| 1,746,464 | 2/1930 | Fischer et al. . |
| 1,798,288 | 3/1931 | Witzel et al. . |
| 2,247,087 | 6/1941 | Herbert ................................. 260/449 |
| 2,468,494 | 4/1949 | Griffin, Jr. .......................... 260/449.6 |

(List continued on next page.)

FOREIGN PATENT DOCUMENTS

| | | |
|---|---|---|
| 17172/92 | 12/1992 | (AU) . |
| 29777/92 | 6/1993 | (AU) . |
| 414019 | 2/1936 | (BE) . |
| 0 212 755 | 3/1987 | (EP) . |
| 0 103 914 | 1/1988 | (EP) . |
| 0 261 771 | 3/1988 | (EP) . |
| 0 497 425 A1 | 8/1992 | (EP) . |
| 0 501 331 B1 | 9/1992 | (EP) . |
| 0 503 482 B1 | 9/1992 | (EP) . |
| 0 516 441 A1 | 12/1992 | (EP) . |
| 0 601 886 A1 | 6/1994 | (EP) . |
| 922493 | 6/1947 | (FR) . |
| 2103647B | 2/1983 | (GB) . |

(List continued on next page.)

OTHER PUBLICATIONS

PCT International Search Report mailed Oct. 17, 1997 re PCT/US97/10733.
PCT International Search Report mailed Oct. 24, 1997 re PCT/US97/10732.
PCT International Search Report mailed Jun. 11, 1997 re PCT/US97/03729.

(List continued on next page.)

*Primary Examiner*—Marian C. Knode
*Assistant Examiner*—Basia Ridley
(74) *Attorney, Agent, or Firm*—Baker Botts L.L.P.

(57) ABSTRACT

A system for converting light hydrocarbons to heavier hydrocarbons having a synthesis gas production unit and a hydrocarbon synthesis unit. For one application the synthesis gas production unit includes a turbine unit with a compression section, an autothermal reformer fluidly coupled to the compression section for producing synthesis gas and combusting at least a portion the gas therein, and an expansion section of the turbine unit fluidly coupled to the autothermal reformer for developing energy from the output of the autothermal reformer. A water separation unit is preferably fluidly coupled to the synthesis gas production unit for removing water from the synthesis gas. The water is directed to an oxygen/hydrogen separator to produce oxygen and hydrogen. Another water separation unit may also be coupled to the output from the hydrocarbon synthesis unit for removing water from the heavier hydrocarbons and directing the water to the oxygen/hydrogen separator.

14 Claims, 4 Drawing Sheets

U.S. PATENT DOCUMENTS

| | | | |
|---|---|---|---|
| 2,472,427 | 6/1949 | Johnson | 260/449.6 |
| 2,486,243 | 10/1949 | Atwell | 260/449.6 |
| 2,518,337 | 8/1950 | Krebs | 260/449 |
| 2,552,308 | 5/1951 | Buchmann et al. | 260/449.6 |
| 2,552,737 | 5/1951 | Rees | 48/214 |
| 2,579,828 | 12/1951 | Johnson | 260/449.6 |
| 2,583,611 | 1/1952 | Sullivan, Jr. | 260/449.6 |
| 2,615,911 | 10/1952 | Williams | 260/449.6 |
| 2,617,709 | 11/1952 | Cornell | 23/1 |
| 2,640,843 | 6/1953 | Hill et al. | 260/449.6 |
| 2,660,032 | 11/1953 | Rosenthal | 60/39.02 |
| 2,686,195 | 8/1954 | McAdams et al. | 260/449.6 |
| 3,549,335 | 12/1970 | Grotz, Jr. | 23/288 |
| 3,673,218 | 6/1972 | Cairns et al. | 260/345.2 |
| 3,866,411 | 2/1975 | Marion et al. | 60/39.02 |
| 3,868,817 | 3/1975 | Marion et al. | 60/39.02 |
| 3,920,579 | 11/1975 | Slater | 252/373 |
| 3,958,625 | 5/1976 | Wentorf, Jr. | 165/2 |
| 3,959,972 | 6/1976 | Rudolph et al. | 60/651 |
| 3,986,349 | 10/1976 | Egan | 60/39.02 |
| 4,048,250 | 9/1977 | Garwood et al. | 260/683 |
| 4,067,190 | 1/1978 | Hamm et al. | 60/39.69 |
| 4,074,981 | 2/1978 | Slater | 48/197 |
| 4,075,831 | 2/1978 | McGann | 60/39.05 |
| 4,092,825 | 6/1978 | Egan | 60/39.02 |
| 4,121,912 | 10/1978 | Barber et al. | 48/197 |
| 4,132,065 | 1/1979 | McGann | 60/39.02 |
| 4,147,456 | 4/1979 | Klass | 405/210 |
| 4,158,637 | 6/1979 | Jones | 208/499 |
| 4,158,680 | 6/1979 | McGann | 261/149 |
| 4,184,322 | 1/1980 | Paull et al. | 60/39.02 |
| 4,309,359 | 1/1982 | Pinto | 518/705 |
| 4,315,893 | 2/1982 | McCallister | 422/109 |
| 4,338,292 | 7/1982 | Duranleau | 423/656 |
| 4,341,069 | 7/1982 | Bell et al. | 60/39.02 |
| 4,345,915 | 8/1982 | Vakil et al. | 48/197 |
| 4,372,920 | 2/1983 | Zardi | 422/148 |
| 4,423,022 | 12/1983 | Albano et al. | 423/360 |
| 4,423,156 | 12/1983 | Büssemeier et al. | 518/717 |
| 4,434,613 | 3/1984 | Stahl | 60/39.07 |
| 4,481,305 | 11/1984 | Jorn et al. | 518/705 |
| 4,492,085 | 1/1985 | Stahl et al. | 60/649 |
| 4,522,939 | 6/1985 | Minderhoud et al. | 502/242 |
| 4,524,581 | 6/1985 | Cascone et al. | 60/39.02 |
| 4,528,811 | 7/1985 | Stahl | 60/39.07 |
| 4,549,396 | 10/1985 | Garwood et al. | 60/39.02 |
| 4,579,985 | 4/1986 | Minderhoud et al. | 585/310 |
| 4,579,986 | 4/1986 | Sie | 585/324 |
| 4,587,008 | 5/1986 | Minderhoud et al. | 208/109 |
| 4,618,451 | 10/1986 | Gent | 252/373 |
| 4,640,766 | 2/1987 | Post et al. | 208/111 |
| 4,678,723 | 7/1987 | Wertheim | 429/17 |
| 4,681,701 | 7/1987 | Sie | 252/373 |
| 4,732,092 | 3/1988 | Gould | 110/229 |
| 4,755,536 | 7/1988 | Mauldin et al. | 518/709 |
| 4,778,826 | 10/1988 | Jezl et al. | 518/703 |
| 4,833,140 | 5/1989 | Weber et al. | 514/343 |
| 4,833,170 | 5/1989 | Agee | 518/703 |
| 4,869,887 | 9/1989 | Van Dijk | 423/359 |
| 4,894,205 | 1/1990 | Westerman et al. | 422/197 |
| 4,919,909 | 4/1990 | Lesur et al. | 423/360 |
| 4,946,660 | 8/1990 | Denny et al. | 423/230 |
| 4,973,453 | 11/1990 | Agee | 422/190 |
| 4,999,029 | 3/1991 | Lueth et al. | 48/197 |
| 5,000,004 | 3/1991 | Yamanaka et al. | 60/723 |
| 5,026,934 | 6/1991 | Bains et al. | 585/314 |
| 5,028,634 | 7/1991 | Fiato | 518/707 |
| 5,048,284 | 9/1991 | Lywood et al. | 60/39.02 |
| 5,080,872 | 1/1992 | Jezl et al. | 422/201 |
| 5,126,377 | 6/1992 | Bessell | 518/714 |
| 5,177,114 | 1/1993 | Van Dijk et al. | 518/703 |
| 5,245,110 | 9/1993 | Van Dijk et al. | 585/946 |
| 5,295,350 | 3/1994 | Child et al. | 60/39.02 |
| 5,295,356 | 3/1994 | Billy | 62/20 |
| 5,324,335 | 6/1994 | Benham et al. | 44/452 |
| 5,472,986 | 12/1995 | van Dijk | 518/705 |
| 5,477,924 | 12/1995 | Pollack | 166/357 |
| 5,500,449 | 3/1996 | Benham et al. | 518/700 |
| 5,504,118 | 4/1996 | Benham et al. | 518/719 |
| 5,506,272 | 4/1996 | Benham et al. | 518/700 |
| 5,520,891 | 5/1996 | Lee | 422/200 |
| 5,543,437 | 8/1996 | Benham et al. | 518/700 |
| 5,733,941 | 3/1998 | Waycuilis | 518/703 |
| 5,861,441 | 1/1999 | Waycuilis | 518/703 |

FOREIGN PATENT DOCUMENTS

| | | |
|---|---|---|
| 2139644 | 11/1984 | (GB) . |
| 60-007929 | 1/1985 | (JP) . |
| 4-364142 | 12/1992 | (JP) . |
| WO 86/05775 | 10/1986 | (WO) . |
| WO 93/06041 | 4/1993 | (WO) . |
| WO 95/24961 | 9/1995 | (WO) . |

OTHER PUBLICATIONS

PCT International Search Report mailed Feb. 25, 1998 re PCT/US97/19722.

PCT International Search Report mailed Jan. 29, 1999 re PCT/US98/21214.

"Kinetics of the Fischer–Tropsch–Synthesis using a Nitrogen–Rich Synthesis Gas" by Kuntze, et al., *Oil Gas—European Magazine* Jan. 1995.

"A New Concept for the Production of Liquid Hydrocarbons from Natural Gas in Remote Areas" by Hedden, et al., *Oil Gas—European Magazine* Mar. 1994.

"Production of Synthesis Gas by Catalytic Partial Oxidation of Methane with Air" by Jess, et al., *Oil Gas—European Magazine* Apr. 1994.

"Improve Syngas Production using Autothermal Reforming" by Christensen, et al., *Hydrocarbons Processing*/Mar. 1994.

"The Mother Lode of Natural Gas" by Monastersky, *Science New vol. 150*, Nov. 9, 1996.

"The Fischer–Tropsch Synthesis" by R.R. Anderson, *Academic Press* 1984.

"Chemicals Produced in a Commercial Fischer–Tropsch Process" by Dry, *1987 American Chemical Society*.

"The Syntroleum Process"—no date.

"Gasoline from Natural Gas" by Keith—no date.

"Autothermal Reforming," *Hydrogen Processing*, Apr. 1984.

"Produce Diesel from Gas," *Hydrocarbon Processing*, May 1983.

Make Syn Gas by Partial Oxidation by Reed, et al., *Hydrocarbons Processing*, Sep. 1979.

"Malaysia, Shell Mull Gas to Products Project," *Oil & Gas Journal*, Sep. 16, 1985.

"Process Makes Mid–Distillates From Natural Gas," *Oil & Gas Journal*, Feb. 17, 1986.

"The Magic of Designer Catalysts" by Bylinsky, *Fortune*, May 27, 1985.

"Conversion of Natural Gas to Liquid Fuels" by Alden, *The Oil & Gas Journal*, Nov. 9, 1946.

"Fischer–Tropsch Synthesis in Slurry Phase" by Schlesinger, *Industrial and Engineering Chemistry*, Jun. 1951.

"Advances in Low Temperature Fischer–Tropsch Synthesis" by Jager, et al., *Catalysis Today* 1995.

"Fischer–Tropsch Processes Investigated at the Pittsburgh Energy Technology Center since 1944" by Baird, et al., *Ind. Eng. Chem. Prod. Res. Dev.* 1980.

SYSTEM FOR CONVERTING LIGHT HYDROCARBONS TO HEAVIER HYDROCARBONS WITH SEPARATION OF WATER INTO OXYGEN AND HYDROGEN

CROSS REFERENCE TO RELATED APPLICATIONS:

This application is a divisional of U.S. application Ser. No. 09/168,195, filed Oct. 7, 1998 by Mark A. Agee and Larry J. Weick, entitled "System And Method For Converting Light Hydrocarbons to Heavier Hydrocarbons With Separation of Water Into Oxygen And Hydrogen", now U.S. Pat. No. 6,011,073. This application claims the benefit of provisional patent application Serial No. 60/061,666, filed Oct. 10, 1997, and entitled "System and Method for Converting Light Hydrocarbons to Heavier Hydrocarbons with Separation of Water into Oxygen and Hydrogen", now U.S. Pat. No. 6,011,073.

TECHNICAL FIELD OF THE INVENTION

The present invention relates to synthesis gas production and more particularly to a system and method for converting light hydrocarbons to heavier hydrocarbons with separation of water to produce oxygen and hydrogen.

BACKGROUND OF THE INVENTION

The term synthesis gas and syngas are frequently used to describe a mixture of gases prepared as feedstock for a chemical reaction. One example is a gas mixture of carbon monoxide and hydrogen which may be used as a feedstock or synthesis gas supplied to various reactions for making hydrocarbon compounds. Another example is a gas mixture of hydrogen and nitrogen which may be used as a feedstock or synthesis gas to make ammonia. A mixture of carbon monoxide and hydrogen is often used as a feedstock or synthesis gas for production of hydrocarbon compounds by a Fischer-Tropsch reaction which will be described later in more detail. U.S. Pat. No. 4,973,453, to Kenneth Agee, entitled Apparatus for the Production of Heavier Hydrocarbons from Gaseous Light Hydrocarbons, and U.S. Pat. No. 4,833,170, to Kenneth Agee, entitled Process and Apparatus for the Production of Heavier Hydrocarbons From Gaseous Light Hydrocarbons, provide information concerning synthesis gas and typical Fischer-Tropsch reactions. Both of these patents are incorporated by reference for all purposes.

A Fischer-Tropsch reaction is generally very exothermic and temperature sensitive. Therefore, temperature control is normally required to maintain a desired hydrocarbon product output. A Fischer-Tropsch reaction can be characterized by the following general formula:

At relatively low to medium pressures (near atmospheric to 600 psig) and temperatures in a range from about 300° F. to 600° F., both saturated and unsaturated hydrocarbons can be produced. Numerous catalysts have been used in carrying out Fischer-Tropsch reactions.

Three basic methods have been employed for producing synthesis gas for use as a feedstock in a Fischer-Tropsch reaction. The methods are steam reforming wherein one or more light hydrocarbons such as methane gas are reacted with steam over a catalyst to form carbon monoxide and hydrogen, partial oxidation wherein one or more light hydrocarbons such as methane gas are combusted substoichiometrically to form carbon monoxide and hydrogen and autothermal reforming which is a combination of steam reforming and partial oxidation. Steam reforming is normally an endothermic reaction. Partial oxidation and autothermal reforming normally are both exothermic reactions.

The steam reforming reaction of methane to produce synthesis gas may be represented by the following general formula:

A catalyst containing nickel is often utilized. The hydrogen to carbon monoxide ratio of the synthesis gas produced by steam reforming of methane is approximately 3:1.

Partial oxidation of methane to produce synthesis gas may be represented by the following general formula:

$$CH_4 + \tfrac{1}{2}O_2 \rightarrow CO + 2H_2$$

Such partial oxidation is typically carried out using relatively high purity oxygen which may be expensive in comparison with other methods to form synthesis gas. A catalyst may or may not be used. The hydrogen to carbon monoxide ratio of the synthesis gas produced by partial oxidation of methane is approximately 2:1.

For some applications a combination of partial oxidation and steam reforming, known as autothermal reforming, may be used to produce synthesis gas. Air is generally used to provide oxygen for the associated partial oxidation reaction. U.S. Pat. No. 2,552,308 to F. J. Buchmann, et al., entitled Low-Pressure Hydrocarbon Synthesis Process, and U.S. Pat. No. 2,686,195 to D. R. McAdams, et al., entitled Hydrocarbon Synthesis, disclose low pressure hydrocarbon synthesis processes wherein autothermal reforming with air produces synthesis gas for a Fischer-Tropsch reaction. Both patents are incorporated by reference for all purposes. During an autothermal reforming reaction, the exothermic heat from the associated partial oxidation reaction may be used to provide heat required for the associated endothermic steam reforming reaction. An autothermal reforming process can be carried out in a relatively inexpensive refractory lined carbon steel vessel with generally lower costs as compared to partial oxidation in pure oxygen.

An autothermal reforming reaction typically produces synthesis gas with a lower hydrogen to carbon monoxide ratio than steam reforming. As previously noted, steam reforming of methane results in a ratio of about 3:1 while partial oxidation of methane results in a ratio of about 2:1. The optimum ratio for synthesis gas supplied to a Fischer-Tropsch reaction carried out at low to medium pressures over a cobalt based catalyst is approximately 2:1. When the feed input to an autothermal reforming process is a mixture of light hydrocarbons such as a natural gas with a relatively high methane content, additional controls are generally required to maintain the ratio of hydrogen to carbon monoxide in the synthesis gas produced by the autothermal reforming process at the optimum ratio of approximately 2:1.

Most of the currently available processes for producing synthesis gas from light hydrocarbons such as a natural gas also produce a residual gas stream. For some applications the residual gas stream may be used to provide energy to carry out the process of generating synthesis gas. For other applications the residual gas stream may be used to provide energy for further reactions to produce selected heavier hydrocarbons from the synthesis gas. Typically, several additional components and/or process steps are required for effective use of such residual gas.

It is desirable to generate synthesis gas for a Fischer-Tropsch reaction or any other reaction with as much thermal efficiency and at as low a cost as possible. The ability to develop an overall process with low capital expenses and low operating costs may be an imperative for development of effective commercial systems to produce relatively heavy hydrocarbons from lightweight gaseous hydrocarbons.

SUMMARY OF THE INVENTION

In accordance with teachings of the present invention, a system and method are provided for converting light, gaseous hydrocarbons into heavier hydrocarbons with separation of water into oxygen and hydrogen. The present invention provides the ability to enrich the oxygen content of air supplied to an autothermal reforming process for generating synthesis gas in an efficient, cost-effective manner. The present invention also provides a source of hydrogen which may be used during the process of generating synthesis gas and/or may be used in other process steps associated with producing the desired heavier hydrocarbons. Alternatively, the present invention provides a source of relatively pure oxygen for use in a partial oxidation reaction to produce synthesis gas.

According to one aspect of the present invention, a system for converting light hydrocarbons to heavier hydrocarbons includes a synthesis gas production unit and a hydrocarbon synthesis unit with one or more cooler/separators to remove water from either the synthesis gas and/or the heavier hydrocarbons. An oxygen/hydrogen separator is also provided for use in decomposing the water into oxygen and hydrogen which may be used in the synthesis gas production unit and/or the hydrocarbon synthesis unit as desired.

According to another aspect of the present invention, a system for converting light hydrocarbons to heavier hydrocarbons includes a synthesis gas production unit having a turbine and a synthesis gas generator fluidly coupled with each other to produce synthesis gas. Residual gas and/or a portion of the synthesis gas may be used to power the turbine. An oxygen/hydrogen separator may also receive energy from the turbine for use in decomposing any water produced by the system into oxygen and hydrogen which may be supplied to the synthesis gas production unit and/or the hydrocarbon synthesis unit as desired.

Technical advantages of the present invention include separating water into hydrogen and oxygen which eliminates the requirement to dispose of any water produced by converting light hydrocarbons into heavier hydrocarbons. Also, supplying oxygen obtained from any water produced by the process of converting light hydrocarbons into heavier hydrocarbons may be used to improve the efficiency and/or reduce the cost of generating synthesis gas by either partial oxidation reactions or autothermal forming reactions.

BRIEF DESCRIPTION OF THE DRAWINGS

For a more complete understanding of the present invention and its advantages, reference is now made to the following description taken in conjunction with the accompanying drawings in which.

DETAILED DESCRIPTION OF THE INVENTION

The preferred embodiments of the present invention and its advantages are best understood by referring to FIGS. 1–4 of the drawings, like numerals being used for like and corresponding parts of the various drawings.

Figure 1:
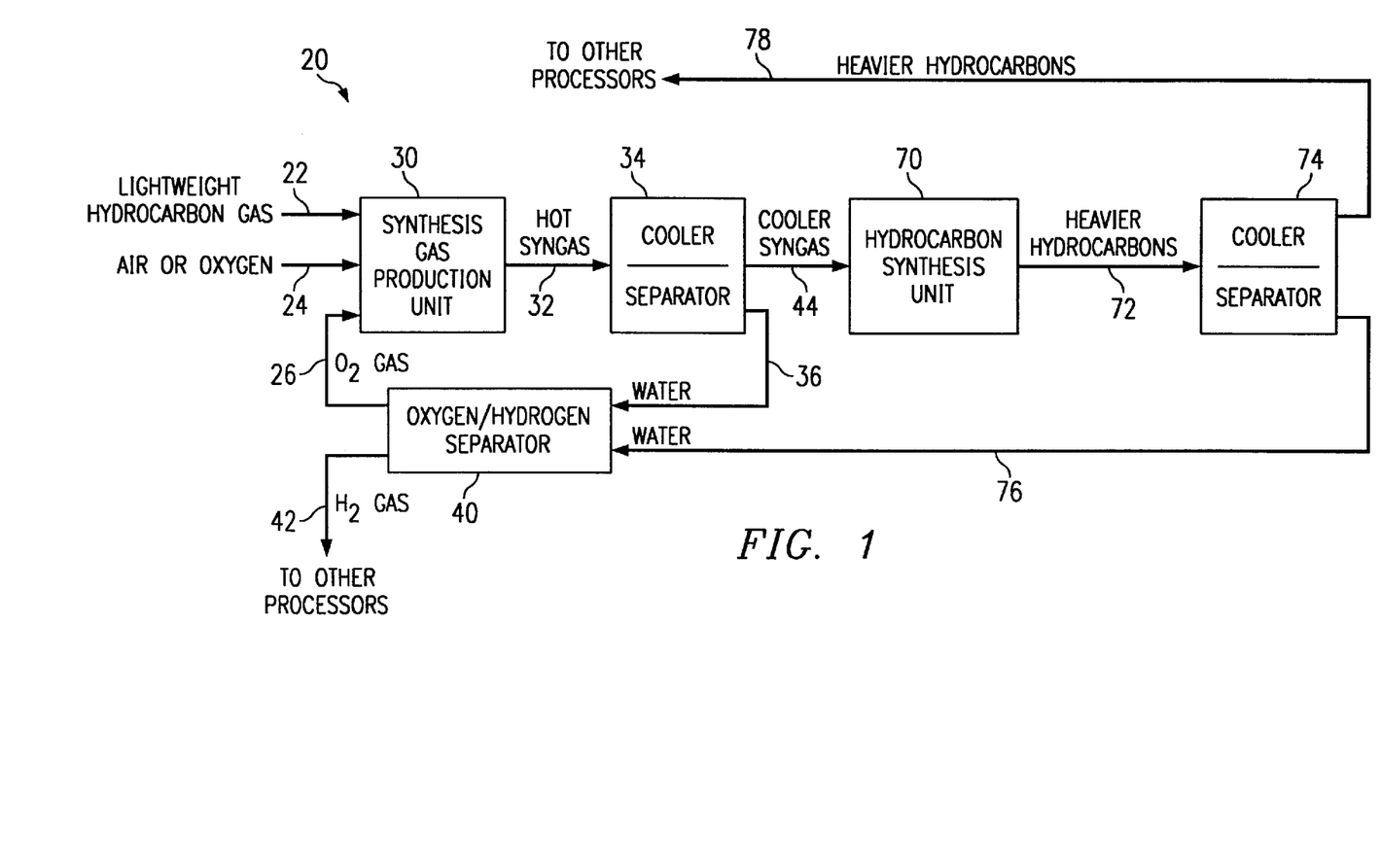
FIG. 1 is a schematic block diagram of a system incorporating teachings of the present invention for converting light, gaseous hydrocarbons to heavier hydrocarbons along with separation of any water produced during the hydrocarbon conversion process into oxygen and hydrogen.

Referring now to FIG. 1, system 20 for converting light hydrocarbons to heavier hydrocarbons is shown. System 20 includes synthesis gas production unit 30 and hydrocarbon synthesis unit 70. Depending upon various operating parameters such as the supply of light hydrocarbons available as an input to system 20 and the desired heavier hydrocarbon output from system 20, reactions such as steam reforming, partial oxidation and autothermal reforming may be used by synthesis gas production unit 30 to generate a desired synthesis gas from lightweight, gaseous hydrocarbons. Hydrocarbon synthesis unit 70 may have one or more hydrocarbon reactors which use various reactions such as Fischer-Tropsch, methanol production or dimethyl ether (DME) production to convert the synthesis gas to the desired heavier hydrocarbons. Fractionation units and other types of hydrocarbon reactors (not expressly shown) may be included within hydrocarbon synthesis unit 70 or may be separate processing steps downstream from hydrocarbon synthesis unit 70.

For some applications, the input to synthesis gas production unit 30 may be a natural gas stream which is generally a mixture of light molecular weight hydrocarbons such as methane, ethane, propane and butane. A typical natural gas stream may have a composition of approximately eighty-five percent (85%) methane, ten percent (10%) ethane, and the remaining five percent (5%) propane, butane and nitrogen. However, the specific composition of each natural gas stream will vary considerably depending upon the characteristics of the associated underground hydrocarbon reservoir which produced the respective natural gas stream and any pretreatment of the natural gas stream prior to entering synthesis gas production unit 30.

Various inputs such as gaseous lightweight hydrocarbons, air, oxygen, and nitrogen may be supplied to synthesis gas production unit 30 depending upon the type of reaction used to generate the desired synthesis gas. For the example shown in FIG. 1, gaseous lightweight hydrocarbons such as a stream of natural gas are preferably supplied to synthesis gas production unit 30 through conduit 22. Air or oxygen may be supplied to synthesis gas production unit 30 through conduit 24 as required. Also, oxygen produced by separating water into its constituent components, which will be described later in more detail, may be supplied to synthesis gas production unit 30 through conduit 26. For some applications, synthesis gas production unit 30 will preferably generate a mixture of carbon monoxide (CO) and hydrogen ($H_2$).

The output from synthesis gas production unit 30 will generally be a relatively hot stream of synthesis gas which may flow through conduit 32 to first cooler/separator 34. Residual gas (not expressly shown) composed of unreacted light hydrocarbons, nitrogen, oxygen, and carbon dioxide may also often be included in the synthesis gas stream exiting from synthesis gas production unit 30 and will flow through conduit 32 to first cooler/separator 34. Within first cooler/separator 34, liquids such as water may be condensed and separated from the synthesis gas. First cooler/separator 34 will typically have at least two outputs, a mixture of synthesis gas and any residual gas and liquids such as water.

Condensed liquids such as water preferably flow from first cooler/separator 34 through conduit 36 to oxygen/hydrogen separator 40. Various processes such as electrolysis may be used to decompose water into its constituent elements oxygen and hydrogen within separator 40. Any liquids other than water flowing through conduit 36 are preferably removed prior to reaching oxygen/hydrogen separator 40.

For some applications, oxygen may be directed through conduit 26 to synthesis gas production unit 30. Supplying oxygen from separator 40 to synthesis gas production unit 30 will generally decrease the overall cost of operating system 20, and may improve the energy efficiency of system 20. Supplying oxygen to synthesis gas production unit 30 is particularly beneficial when partial oxidation reactions or autothermal reforming reactions occur within synthesis gas production unit 30 to generate the desired synthesis gas.

Air is preferably supplied to synthesis gas production unit 30 through input conduit 24 if autothermal reforming reactions are used to generate the desired synthesis gas. Relatively pure oxygen may be supplied to synthesis gas production unit 30 through input conduit 24 if only partial oxidation reactions are used to generate the desired synthesis gas. Supplying oxygen to synthesis gas production unit 30 from oxygen/hydrogen separator 40 will reduce the amount of pure oxygen which must be supplied when partial oxidation reactions are occurring therein. Alternatively, providing oxygen to synthesis gas production unit 30 will improve the efficiency of air supplied to synthesis gas production unit 30 when autothermal reforming reactions are being used to generate the desired synthesis gas.

Hydrogen produced by oxygen/hydrogen separator 40 may also be supplied through conduit 42 to other processes associated with converting light hydrocarbons to heavier hydrocarbons such as hydrocracking of heavier hydrocarbon molecules. For other applications, hydrogen may be supplied through conduit 42 to synthesis gas production unit 30.

Hydrocarbon synthesis unit 70 may be designed to carry out various types of reactions. For some applications, hydrocarbon synthesis unit 70 may include one or more Fischer-Tropsch reactors to convert synthesis gas supplied thereto into relatively heavy, long chain hydrocarbons. For other applications, hydrocarbon synthesis unit 70 may include a methanol reactor or a dimethyl ether reactor.

For the embodiment shown in FIG. 1, synthesis gas preferably flows from first cooler/separator 34 through conduit 44 to hydrocarbon synthesis unit 70. The design and operation of first cooler/separator 34 will be dependent upon the type of reaction used within hydrocarbon synthesis unit 70 and the desired inputs for efficient operation of hydrocarbon synthesis unit 70. The output from hydrocarbon synthesis unit 70 will typically be a mixture of heavier hydrocarbons produced from the synthesis gas, unreacted synthesis gas, residual gas and other fluids such as water. The output from hydrocarbon synthesis unit 70 is directed through conduit 72 to second cooler/separator 74. Second cooler/separator 74 will preferably have at least two outputs, water and a heavier weight hydrocarbon stream. Water may be directed through conduit 76 to oxygen/hydrogen separator 40. The heavier weight hydrocarbon stream may be directed through conduit 78 to other processes associated with converting light weight hydrocarbons into desired heavier weight hydrocarbons.

For some applications, it may not be desirable to not separate water from the synthesis gas supplied to hydrocarbon synthesis unit 70. For such applications, first cooler/separator 34 may be removed from system 20 and water will remain mixed with the synthesis gas. Water will only be supplied to oxygen/hydrogen separator 40 from cooler/separator 74. System 20 may also include various pumps, compressors, turbines, valves and other flow control devices typically associated with a synthesis gas production unit and a hydrocarbon synthesis unit.

Figure 2:
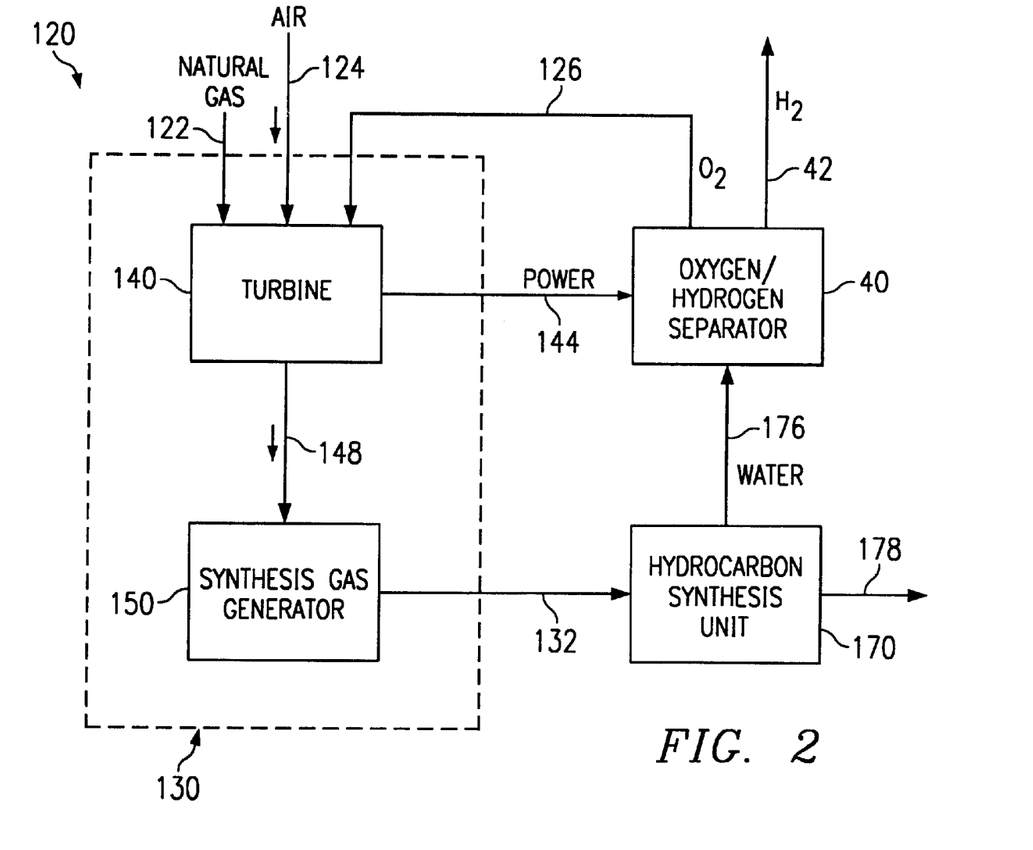
FIG. 2 is a schematic block diagram of a system which includes a synthesis gas generator and hydrocarbon synthesis unit for converting light, gaseous hydrocarbons into heavier hydrocarbons in accordance with one aspect of the present invention.

System 120 incorporating an alternative embodiment of the present invention is shown in FIG. 2. System 120 includes synthesis gas production unit 130 having at least two components, turbine 140 and synthesis gas generator 150. For some applications, the inputs to synthesis gas production unit 130 preferably include a natural gas stream supplied through conduit 122, air supplied through conduit 124, and essentially pure oxygen supplied through conduit 126. A compressor (not expressly shown) may be used to supply compressed air through conduit 124 to turbine 140. Conduit 132 is provided to direct the flow of synthesis gas from synthesis gas generator 150 to hydrocarbon synthesis unit 170. Hydrocarbon synthesis unit 170 preferably converts the synthesis gas to heavier weight hydrocarbons such as syncrude, lubricating oil, methanol, and dimethyl ether (DME), which may be directed through conduit 178 to other processes and/or a storage facility (not expressly shown).

Water is preferably removed from the synthesis gas and/or heavier weight hydrocarbons within hydrocarbon synthesis unit 170. One or more conduits 176 direct water from hydrocarbon synthesis unit 170 to oxygen/hydrogen separator 40. Separator 40 is used to decompose or separate water into its constituent components oxygen ($O_2$) and hydrogen ($H_2$). The hydrogen may be delivered through conduit 42 to other processes associated with treating the heavier hydrocarbons, returned to hydrocarbon synthesis unit 170 and/or supplied as an input to synthesis gas production unit 130. Oxygen is preferably directed from oxygen/hydrogen separator 40 through conduit 126 to synthesis gas production unit 130.

For the embodiment shown in FIG. 2, conduit 126 supplies oxygen to turbine 140 which preferably has multiple inputs including lightweight hydrocarbons such as natural gas supplied through conduit 122, air supplied through conduit 124 and oxygen supplied through conduit 126. For some applications, air, natural gas and oxygen may be mixed with each other and supplied to turbine 124 through a single conduit (not expressly shown). Alternatively, air, natural gas and oxygen may be mixed with each other within turbine 140. The mixture of natural gas, air and oxygen preferably flows through turbine 140 which is fluidly coupled with synthesis gas generator 150 by conduit 148 or other suitable fluid connection. Electrical power and/or mechanical energy may be supplied to oxygen/hydrogen separator 40 from turbine 140 by linkage 144.

For some applications hydrocarbon synthesis unit 170 may include a Fischer-Tropsch reactor with coolers, separators and heat exchangers such as shown in U.S. Pat. Nos. 4,833,170 and 4,973,453. Oxygen/hydrogen separator 40 may include a number of devices and technologies for converting or decomposing water to its constituent components, oxygen ($O_2$) and hydrogen ($H_2$). Electrolysis is one example of various processes which may be satisfactorily used for breaking water down into its component parts. Electrical power may be supplied from turbine 140 via linkage 144 to oxygen/hydrogen separator 40 to produce the desired oxygen and hydrogen.

For one embodiment, electricity is passed through a dilute electrolyte solution, such as a dilute $H_2SO_4$ within oxygen/hydrogen separator 40. $H^+$ ions are attracted to a negative electrode (cathode), where they gain electrons to form H atoms, which join to form $H_2$ molecules that escape from solution. Although $SO_4^{2-}$ ions are attracted to a positive electrode (anode), they are not involved in the transfer of charge at the anode. Instead, a reaction occurs in which $H_2O$ molecules decompose, replacing the $H^+$ ions lost at the cathode and releasing $O_2$. The net reaction within oxygen/hydrogen separator 40 is the production of $H_2$ and $O_2$ gas from water molecules as represented by the general formula:

$$2H_2O \rightarrow 2H_2 + O_2$$

Other techniques may be used as well. In this regard, U.S. Pat. No. 5,318,684 to Charles Cameron, entitled Systems for the Decomposition of Water, is incorporated by reference for all purposes.

For those applications in which synthesis gas generator 150 uses an autothermal reforming process to produce the desired synthesis gas, supplying oxygen from separator 40 through conduit 126 to turbine 140 will improve the overall operating efficiency of the air supplied to synthesis gas production unit 130. Controlling the ratio of natural gas, air and essentially pure oxygen supplied to synthesis gas production unit 130 may be used to control the ratio of carbon monoxide to hydrogen in the synthesis gas supplied to hydrocarbon synthesis unit 170. For example, if the ratio of hydrogen to carbon monoxide in the synthesis gas provided to hydrocarbon synthesis unit 170 is less than two to one, the supply of oxygen from separator 40 may be increased to increase the amount of hydrogen produced by synthesis gas generator 150. In a similar manner, if an excessive amount of hydrogen is contained in the synthesis gas provided to hydrocarbon synthesis unit 170, the volume of air supplied to turbine 140 may be increased and the supply of oxygen decreased to reduce the amount of hydrogen gas produced by synthesis gas generator 150.

Figure 3:
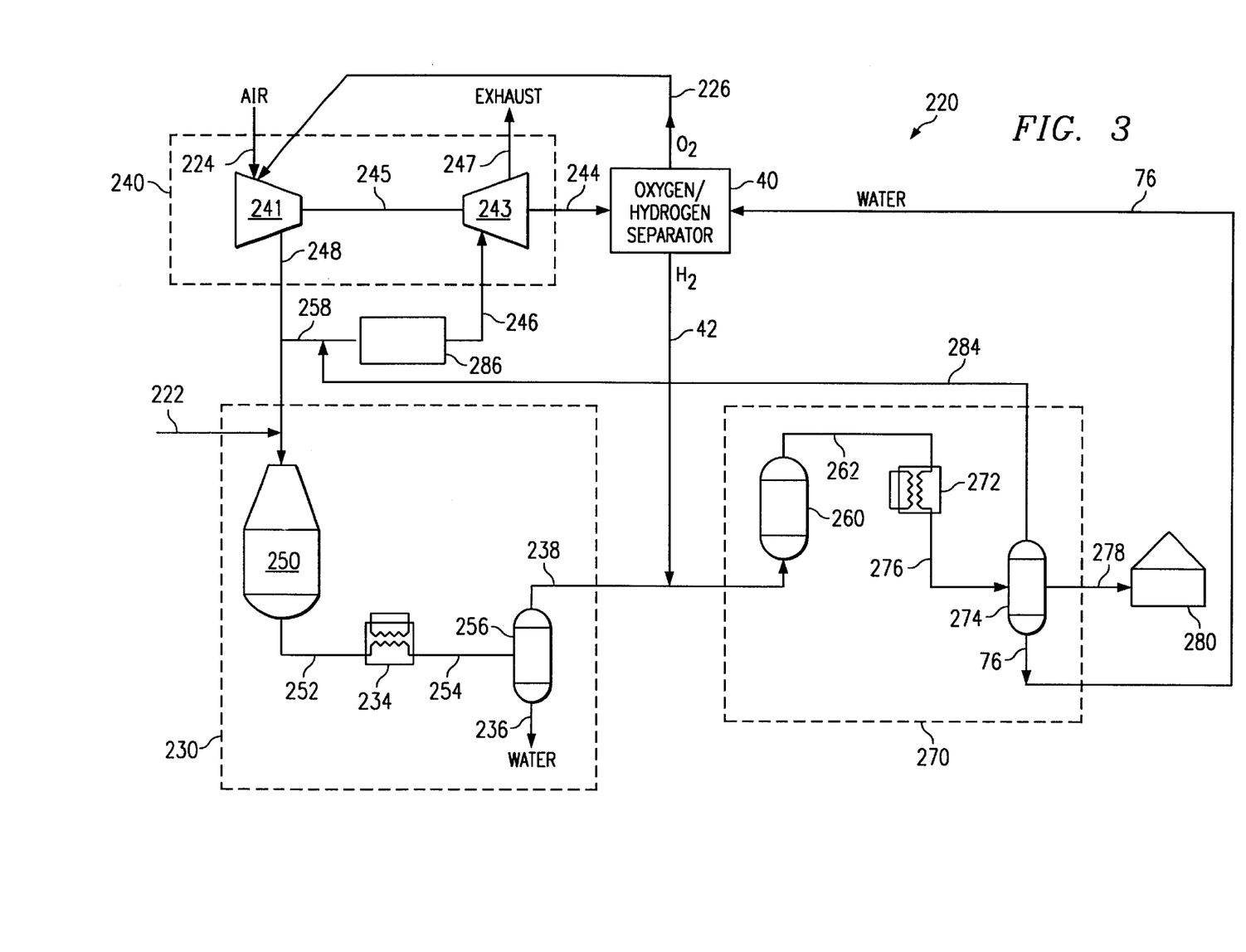
FIG. 3 is a schematic block diagram of another system which includes an autothermal reactor for generating synthesis gas from light, gaseous hydrocarbons and a Fischer-Tropsch reactor for converting the synthesis gas to heavier hydrocarbons according to another aspect of the present invention.

Referring now to FIG. 3, system 220 combines synthesis gas production unit 230 with hydrocarbon synthesis unit 270, gas turbine unit 240 and oxygen/hydrogen separator 40. Gas turbine unit 240 includes compressor section 241 and expansion section 243. The power generated by expansion section 243 drives compressor section 241 by means of linkage 245, which may be a shaft. Any excess power beyond the requirements of operating compressor section 241 may be used to generate electricity or drive other equipment such as oxygen/hydrogen separator 40 through linkage 244. Compressor section 241 preferably includes inlet or conduit 224 to supply air thereto. Compressor section 241 also has outlet conduit 248 for compressed air flowing from turbine unit 240. Expansion section 243 has inlet conduit 246 and outlet conduit 247. Compressor section 241 preferably provides compressed air to synthesis gas production unit 230 through outlet conduit 248.

Synthesis gas production unit 230 may have a number of configurations, but in the specific embodiment shown, includes synthesis gas generator 250, which may be an autothermal reforming reactor. A stream of gaseous lightweight hydrocarbons, such as natural gas, is preferably delivered to synthesis gas generator 250 by inlet conduit 222. In some instances, it may be desirable to use natural gas containing elevated levels of selected components, e.g., $N_2$, $CO_2$ He, etc. to reduce the BTU value of the natural gas supplied through conduit 222. Synthesis gas production unit 230 may also include one or more heat exchangers 234, which in the embodiment shown functions as a cooler for reducing the temperature of the synthesis gas flowing through outlet conduit 252 of synthesis gas generator 250. Heat exchanger 234 delivers its output through conduit 254 to separator 256. Liquids such as water are preferably removed from separator 256 through outlet conduit or drain 236. It may be desirable in some instances to communicate the water in conduit 236 to turbine expansion section 243 as steam or to oxygen/hydrogen separator 40. Cooled synthesis gas exits separator 256 through outlet conduit 238 and is delivered to hydrocarbon synthesis unit 270. In addition to synthesis gas from synthesis gas production unit 230, hydrogen may be delivered to hydrocarbon synthesis unit 270 through conduit 42 from oxygen/hydrogen separator 40.

Hydrocarbon synthesis unit 270 may use various reactions to convert synthesis gas to selected heavier hydrocarbon compounds as previously mentioned, but for this embodiment, preferably includes Fischer-Tropsch reactor 260, which contains an appropriate catalyst. The output of Fischer-Tropsch reactor 260 is delivered to outlet 262 and flows through heat exchanger 272 and separator 274.

The products entering separator 274 flow through inlet conduit 276. Separator 274 directs heavier hydrocarbons to storage tank or container 280 through outlet conduit 278. Additional components such as a conventional fractionation unit (not expressly shown) may be included within system 220 between separator 274 and storage tank 280. Any water withdrawn from separator 274 is preferably delivered to outlet conduit 76 which is coupled with oxygen/hydrogen separator 40. Any residual gas within separator 274 exits through outlet conduit 284.

System 220 preferably includes combustor 286 which receives compressed air from compression section 241. For the embodiment shown in FIG. 3, compressed air flows through conduit 248 to conduit 258, which is connected with conduit 248 between compressor section 241 and synthesis gas generator 250. Compressor section 241 also receives oxygen from separator 40 through conduit 226. The portion of conduit 248 beyond the juncture with conduit 258 preferably delivers compressed air enriched with oxygen to synthesis gas generator 250. Also, any residual gas flowing from separator 274 through conduit 284 is preferably connected to conduit 258 prior to combustor 286.

Various valves and other flow control devices (not expressly shown) may be used to regulate fluid pressure and fluid flow rates in conduits 248, 258 and 284. Conduit 248 and the connection of conduit 284 with conduit 258 may include various types of flow control devices (not explicitly shown) to lower the pressure of compressed air delivered from compressor section 241 to combustor 286 in order to substantially match the pressure of residual gas flowing through conduit 284 as necessary. The output of combustor 286 is delivered to turbine expansion section 243. For some embodiments, combustor 286 may be incorporated as part of gas turbine unit 240. Alternatively, fluid pressure in conduits 248 and/or 284 may be increased by compressors (not expressly shown) to match or exceed the input pressure requirements of combustor 286.

Figure 4:
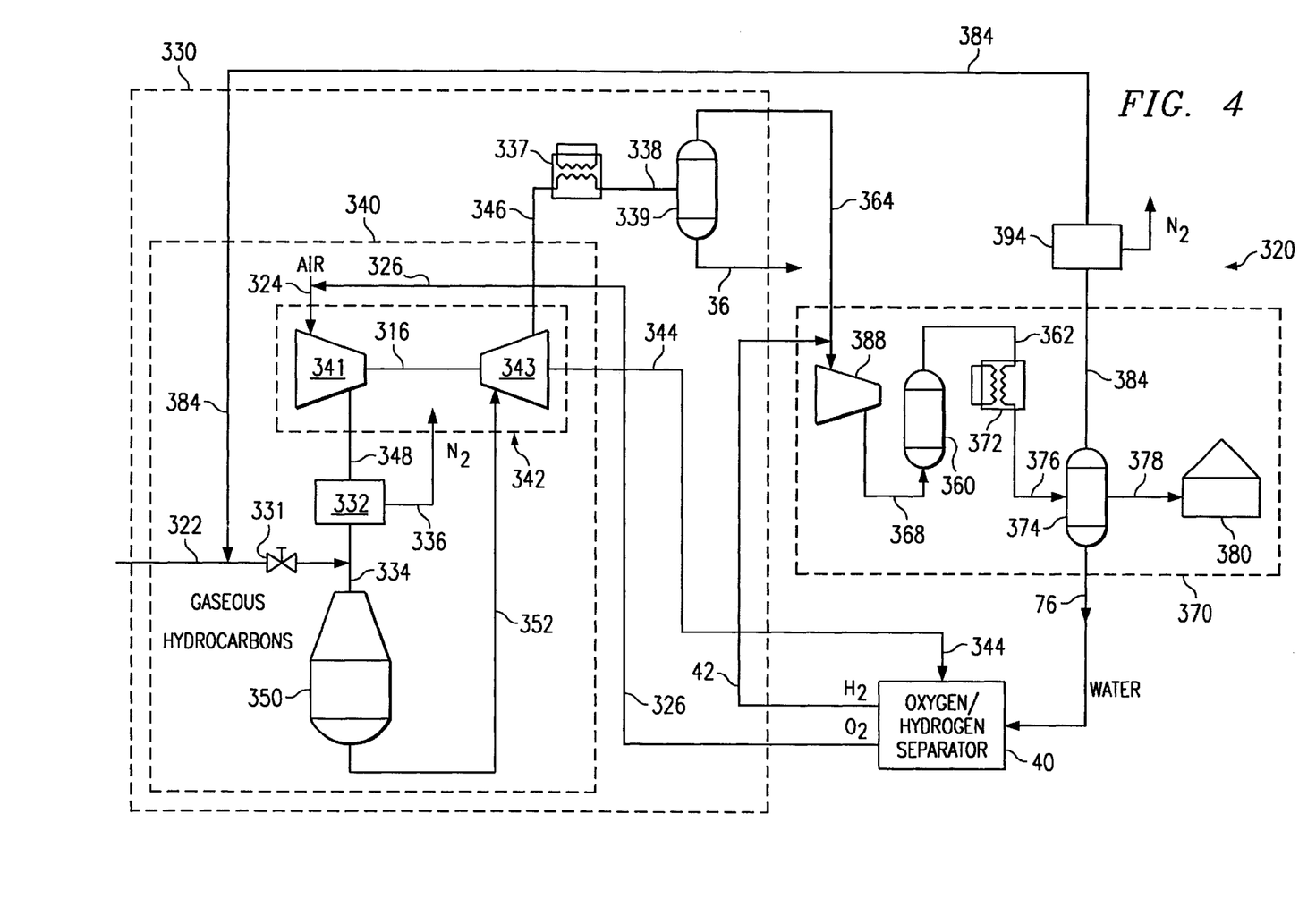
FIG. 4 is a schematic block diagram of still another system for converting light, gaseous hydrocarbons to heavier hydrocarbons along with separation of any water produced during the hydrocarbon conversion process into oxygen and hydrogen according to a further aspect of the present invention.

Referring to FIG. 4, system 320 for converting light hydrocarbons such as natural gas to heavier hydrocarbons such as synthetic crude oil (sometimes referred to as "syncrude") is shown. System 320 includes synthesis gas production unit 330 with autothermal reformer and turbine unit 340 forming a portion thereof. System 320 for converting light hydrocarbons to heavier hydrocarbons further includes hydrocarbon synthesis unit 370.

Autothermal reformer and turbine unit 340 preferably includes autothermal reforming reactor (ATR) 350 and gas turbine unit 342. Gas turbine unit 342 includes compressor section 341 and expansion turbine section 343. Power generated by expansion section 343 drives compressor section 341 by means of linkage 316, which may be a shaft, and powers oxygen/hydrogen separator 40 through linkage 344. Depending upon the process or processes used within oxygen/hydrogen separator 40, linkage 344 may provide electrical and/or mechanical energy to oxygen/hydrogen separator 40.

Compressor section 341 has inlet conduit 324 through which air is supplied to compressor section 341. Oxygen is preferably delivered through conduit 326 from oxygen/hydrogen separator 40 to compressor section 341. Outlet conduit 348 receives compressed air enriched with oxygen from compressor section 341. Expansion section 343 has inlet conduit 352 and outlet conduit 346. As explained later in more detail, expansion section 343 discharges synthesis gas into outlet conduit 346.

Autothermal reformer 350 produces synthesis gas and also serves as a combustor for gas turbine unit 342. Compressor section 341 provides compressed air enriched with oxygen through outlet conduit 348 to first separator 332 which will be described later in more detail. After flowing through first separator 332, compressed air enriched with oxygen is delivered by way of conduit 334 to ATR 350. In addition, gaseous light hydrocarbons, such as associated with a typical natural gas stream, are delivered from conduit 322 to ATR 350. Residual gas from hydrocarbon synthesis unit 370 may also be delivered through conduit 384 into conduit 322 and then to ATR 350.

One factor affecting the performance of many gas turbines is the balancing of axial loads on a shaft coupling the associated compressor section and expansion section. The present invention may realize efficient results by the inclusion of thrust bearings in gas turbine unit 342 that allow for a substantial imbalance in forces between compressor section 341 and expansion section 343. In order to use a preexisting turbine with more conventional thrust bearings, one aspect of the present invention includes balancing of axial loads within gas turbine unit 342 to meet the turbine manufacturer's specifications. This may be accomplished by using first separator 332 or by bleeding compressed air as will be described later in more detail. Turbine balancing may be thought of as balancing the total mass that is received in the compressor section with the total mass received by the expansion section.

For the embodiment shown in FIG. 4, expansion section 343 receives additional mass from light hydrocarbons flowing through conduit 322 and residual gas flowing through conduit 384 to autothermal reforming reactor 350 which would generally cause an imbalance, as compared to mass flow through compressor section 341. To address this potential imbalance in mass flow, first separator 332 may remove mass by separating out nitrogen or bleeding off a portion of the compressed air through conduit 336 as suggested by FIG. 4. First separator 332 may include separation technology such as a membrane or carbon absorption or any other technique suitable for the removal of nitrogen or other substances which are not needed for the reactions within ATR 350 or hydrocarbon synthesis unit 370. For gas turbine units with sufficiently strong thrust bearings in compressor section 341 and expansion section 343, first separator 332 or a device for bleeding compressed air may not be required.

ATR 350 receives compressed air enriched with oxygen from conduit 334 along with gaseous light hydrocarbons and residual gas from conduits 322 and 384, respectively. ATR 350 will then reform and at least partially combust the light hydrocarbons to generate synthesis gas flowing through conduit 352. The volume of input gas delivered to ATR 350 and synthesis gas generated by ATR 350 may be significantly higher than what would normally be expected from a conventional turbine combustor. ATR 350 may not fully combust all input light hydrocarbons but because of the increased total volume of gas delivered to ATR 350, the same amount of energy may be produced by expansion section 343. The gas mixture exiting from ATR 350 through conduit 352 will generally have an exit temperature within an acceptable range for input into expansion section 343. Input gas delivered to ATR 350 may be controlled to generate synthesis gas with very little or no oxygen and the optimum carbon monoxide to hydrogen ratio. One or more control valves, which are represented by control valve 331, may be used to control the ratio of gaseous light hydrocarbons to compressed air enriched with oxygen entering ATR 350.

Outlet conduit 346 from expansion section 341 directs a mixture of synthesis gas, residual gas and steam to heat exchanger or cooler 337. Fluid flow continues from cooler 337 through conduit 338 to second separator 339. Cooler 337 cools the gas mixture exiting from expansion section 343 which will condense at least some water contained in the gas mixture. For those applications in which hydrocarbon synthesis unit 370 includes a Fischer-Tropsch reactor, it may be preferable to remove as much water as possible from the mixture of synthesis gas, residual gas and steam exiting from expansion section 343. The removal of such water is particularly desirable if hydrocarbon synthesis unit 370 includes booster compressor 388. Outlet conduit or drain 36 is provided to remove water from second separator 339. For some applications outlet conduit or drain 36 may direct the water to oxygen/hydrogen separator 40.

The mixture of synthesis gas and residual gas exiting from second separator 339 is directed through conduit 364 to compressor 388 within hydrocarbon synthesis unit 370. For the embodiment of the present invention as shown in FIG. 4, hydrogen from oxygen/hydrogen separator 40 is preferably supplied from conduit 42 to conduit 364 and then flows into compressor 388. For some applications the pressure of the gas mixture exiting from expansion section 343 of gas turbine unit 342 may be lower than the desired pressure for a Fischer-Tropsch reaction. Therefore, compressor 388 is provided to increase the pressure of synthesis gas supplied to Fischer-Tropsch Reactor 360 to the desired optimum pressure for efficient synthesis of the desired heavier hydrocarbons.

Compressor 388 may receive mechanical energy and/or electrical energy from gas turbine unit 342. Alternatively, compressor 388 may have its own combustor and expansion section (not expressly shown). One of the benefits of the present invention includes the ability to use a portion of the natural gas supplied to ATR 350 or to use any excess energy created by gas turbine engine unit 342 to operate compressor 388 and/or oxygen/hydrogen separator 40 as required.

In addition to increasing the pressure of the gas mixture flowing therethrough, compressor 388 may also increase the temperature of the gas mixture to the appropriate range for a Fischer-Tropsch reaction. For one application, the desired input temperature for Fischer-Tropsch reactor 360 may be in the range of 350° F. to 500° F. For those applications in which the temperature of the gas mixture exiting from compressor 388 is less than desired one or more heat exchangers (not expressly shown) may be added between compressor 388 and reactor 360.

Conduit 368 directs the flow of compressed mixture of synthesis gas and any residual gas from compressor 388 to reactor 360. One or more Fischer-Tropsch catalysts may be contained within reactor 360. The output from reactor 360 flows through conduit 362 to heat exchanger 372. From heat exchanger 372 the mixture of heavier hydrocarbons formed by reactor 360 and any residual gas and water flows to third separator 374 through conduit 376.

Within third separator 374, the desired hydrocarbons are separated from any residual gas and liquids such as water. The heavier hydrocarbons are preferably directed through conduit 378 to storage facility 380. Residual gas is directed from third separator 374 through conduit 384 to fourth separator 394 which may include a membrane or carbon absorption centrifugal device or other separation device. For some Fischer-Tropsch reactions, nitrogen is preferably removed from the residual gas flowing through conduit 384. The residual gas flowing through conduit 384 is preferably delivered to ATR 350 as previously described.

Although the present invention and its advantages have been described in detail, it should be understood that various changes, substitutions, and alterations can be made therein without departing from the spirit and scope of the invention as defined by the following claims.

What is claimed is:

1. A system for converting lighter hydrocarbons to heavier hydrocarbons, comprising:
    a synthesis gas production unit for receiving the lighter hydrocarbons and generating a synthesis gas therefrom;
    a hydrocarbon synthesis unit fluidly coupled to the synthesis gas production unit to receive the synthesis gas and to produce the heavier hydrocarbons from the synthesis gas;
    a first separator fluidly coupled with the hydrocarbon synthesis unit to remove at least a portion of water from the heavier hydrocarbons produced by the hydrocarbon synthesis unit; and
    an oxygen/hydrogen separator fluidly coupled with the first separator to receive the water removed in the first separator and to decompose the water into its constituent components of oxygen and hydrogen.

2. The system of claim 1 further comprising a conduit fluidly coupled to the oxygen/hydrogen separator and the synthesis gas production unit for communicating the oxygen from the oxygen/hydrogen separator to the synthesis gas production unit.

3. The system of claim 1 further comprising a conduit fluidly coupled to the oxygen/hydrogen separator and the hydrocarbon synthesis unit for communicating the hydrogen from the oxygen/hydrogen separator to the hydrocarbon synthesis unit.

4. The system of claim 1 further comprising:
    a second separator disposed between the synthesis gas production unit and the hydrocarbon synthesis unit to remove at least a portion of water mixed with the synthesis gas prior to the synthesis gas entering the hydrocarbon synthesis unit; and
    a conduit fluidly coupled to the second separator and the oxygen/hydrogen separator for communicating water from the second separator to the oxygen/hydrogen separator.

5. The system of claim 1 wherein the lighter hydrocarbons supplied to the synthesis gas production unit comprise a natural gas stream and the heavier hydrocarbons produced by the hydrocarbon synthesis unit comprise synthetic crude oil.

6. The system of claim 1 wherein the synthesis gas production unit further comprises:
    a turbine unit having a compression section and an expansion section with a linkage extending between the compression section and the expansion section whereby the expansion section provides power for operating the compression section;
    the compression section having an inlet for receiving air and oxygen from the oxygen/hydrogen separator; and
    an outlet extending from the compression section to a synthesis gas generator whereby a mixture of compressed air enriched with oxygen flows from the compression section to the synthesis gas generator.

7. The system of claim 1 wherein the synthesis gas production unit further comprises a turbine unit with a linkage extending between the turbine unit and the oxygen/hydrogen separator whereby energy from the turbine unit operates the oxygen/hydrogen separator.

8. The system of claim 1 wherein the synthesis gas production unit further comprises an autothermal reforming reactor and the hydrocarbon synthesis unit further comprises a Fischer Tropsch reactor.

9. A system for converting a natural gas stream to heavier hydrocarbons, comprising:
    a synthesis gas production unit for receiving the natural gas and generating a synthesis gas of carbon monoxide and hydrogen;
    a hydrocarbon synthesis unit for receiving the synthesis gas from the synthesis gas production unit;
    a first separator fluidly coupled with the hydrocarbon synthesis unit to remove water from the heavier hydrocarbons produced by the hydrocarbon synthesis unit; and
    an oxygen/hydrogen separator fluidly coupled to the first separator for receiving water from the first separator and decomposing the water into its constituent components of oxygen and hydrogen.

10. The system of claim 9 further comprising at least one conduit fluidly coupled between the oxygen/hydrogen separator and the synthesis gas production unit for communicating the oxygen from the oxygen/hydrogen separator to the synthesis gas production unit.

11. The system of claim 9 further comprising at least one conduit fluidly coupled between the oxygen/hydrogen separator and the hydrocarbon synthesis unit for communicating the hydrogen from the oxygen/hydrogen separator to the hydrocarbon synthesis unit.

12. The system of claim 9 wherein the synthesis gas production unit further comprises;
    a turbine unit having a compression section and an expansion section with a linkage coupling the expansion section with the compression section whereby the expansion section provides energy for operating the compression section;
    the compression section having an inlet that is fluidly coupled to the oxygen/hydrogen separator for receiving air and oxygen from the oxygen/hydrogen separator;

the compression section having an outlet fluidly coupled with an autothermal reforming reactor whereby the compression section provides a mixture of compressed air enriched with oxygen to the autothermal reforming reactor;

at least one conduit for communicating the natural gas stream with the autothermal reforming reactor; and an outlet conduit extending from the autothermal reforming reactor to the expansion section of the turbine unit whereby the autothermal reforming reactor supplies energy in the form of a hot mixture of gases including synthesis gas, unreacted natural gas, and air to the expansion section of the turbine unit.

13. The system of claim 9 wherein the hydrocarbon synthesis unit further comprises a Fischer Tropsch reactor.

14. A system for converting lighter hydrocarbons to heavier hydrocarbons, comprising:

a synthesis gas production unit for receiving the lighter hydrocarbons and generating a synthesis gas therefrom;

a hydrocarbon synthesis unit fluidly coupled with the synthesis gas production unit to receive the synthesis gas and to produce the heavier hydrocarbons from the synthesis gas;

a first separator fluidly coupled with the synthesis gas production unit for removing water from the synthesis gas; and an oxygen/hydrogen separator fluidly coupled with the first separator to receive the water removed in the first separator and to decompose the water into its constituent components of oxygen and hydrogen.

* * * * *